US009462901B2

(12) United States Patent
Dolar et al.

(10) Patent No.: US 9,462,901 B2
(45) Date of Patent: Oct. 11, 2016

(54) PERSONAL VIEWING DEVICE (71) Applicant: ADProducts, LLC, Spokane, WA (US)

(72) Inventors: Ronald E. Dolar, Spokane, WA (US);
Dan C. Cummings, Spokane, WA (US); Russell D. Marshall, Spokane, WA (US); Bobby G. Head, Rathdrum, ID (US); Timothy W. Bardell, Sunnyside, WA (US); Steven M. Albrecht, Sunnyside, WA (US)

(73) Assignee: ADProducts, LLC, Spokane, WA (US)

( * ) Notice: Subject to any disclaimer, the term of this patent is extended or adjusted under 35 U.S.C. 154(b) by 38 days.

(21) Appl. No.: 14/460,766

(22) Filed: Aug. 15, 2014

(65) Prior Publication Data
US 2015/0173533 A1    Jun. 25, 2015

Related U.S. Application Data (60) Provisional application No. 61/918,561, filed on Dec. 19, 2013.

(51) Int. Cl.
*F16M 11/24*      (2006.01)
*A47G 1/16*       (2006.01)
(Continued)

(52) U.S. Cl.
CPC . *A47G 1/16* (2013.01); *A47G 1/02* (2013.01); *A47G 1/24* (2013.01); *A61B 5/0079* (2013.01); *F16M 11/24* (2013.01); *A47G 2001/1673* (2013.01); *F16M 11/22* (2013.01); *G02B 7/182* (2013.01); *G02B 7/1824* (2013.01)

(58) Field of Classification Search
USPC ....... 248/149, 150, 151, 161, 157; 211/85.3, 211/85.24, 197, 204, 206, 175, 13.1
See application file for complete search history.

(56) References Cited

U.S. PATENT DOCUMENTS 1,220,069 A     3/1917  Capdevila
2,017,472 A    10/1935  Re
(Continued)

FOREIGN PATENT DOCUMENTS

AT           371324        6/1983
CN       204698231 U  *  10/2015

OTHER PUBLICATIONS

The PCT Search Report and Written Opinion mailed Apr. 21, 2015 for PCT application No. PCT/US2014/071076, 13 pages.

(Continued)

*Primary Examiner* — Alfred J Wujciak
(74) *Attorney, Agent, or Firm* — Lee & Hayes, PLLC (57) ABSTRACT A portable, freestanding, adjustable, and deconstructable personal viewing device. The personal viewing device may comprise a removably coupled base member, mast member, and branch member. The base member, mast member, and branch member, when coupled, can be freestanding or the base member can be configured to fit under a surface designed for a person in the supine position. The branch member can be configured to hold an appliance, such as a mirror or a flashlight. The branch member can also be configured rotate to allow viewing from a standing, sitting, or supine position. The personal viewing device comprises components that are coupled without the use of fasteners and can be deconstructed with limited dexterity. When deconstructed, the personal viewing device can be transported and reconstructed.

14 Claims, 10 Drawing Sheets (51) Int. Cl.
*A61B 5/00* (2006.01)
*A47G 1/02* (2006.01)
*A47G 1/24* (2006.01)
*F16M 11/22* (2006.01)
*G02B 7/182* (2006.01)

(56) References Cited

U.S. PATENT DOCUMENTS

| | | | |
|---|---|---|---|
| D160,995 S | 11/1950 | Busa | |
| 3,507,402 A * | 4/1970 | Barbee | A47F 5/13 |
| | | | 211/204 |
| 3,509,831 A | 5/1970 | Schnetzer | |
| 3,781,093 A | 12/1973 | Grabijas | |
| D246,016 S | 10/1977 | Brady | |
| D253,323 S | 11/1979 | Blatzer et al. | |
| 4,339,104 A | 7/1982 | Weidman | |
| 4,748,058 A | 5/1988 | Craig, Jr. | |
| 4,860,989 A | 8/1989 | Rose et al. | |
| 5,012,852 A | 5/1991 | Blackhurst | |
| 5,090,648 A * | 2/1992 | Wood, IV | B05B 13/0228 |
| | | | 248/125.3 |
| D324,462 S | 3/1992 | Karnaze | |
| 5,135,191 A | 8/1992 | Schmuhl | |
| 5,337,989 A | 8/1994 | Apple | |
| 5,355,539 A | 10/1994 | Boettger | |
| 5,359,461 A | 10/1994 | Rice | |
| 5,435,620 A * | 7/1995 | Cheng | A47C 4/20 |
| | | | 108/132 |
| 5,556,070 A | 9/1996 | Viebrock | |
| 5,873,552 A * | 2/1999 | Skarp | B62H 3/00 |
| | | | 248/125.8 |
| 6,041,559 A | 3/2000 | Schickert et al. | |
| D438,389 S | 3/2001 | Ross et al. | |
| 6,327,982 B1 | 12/2001 | Jackson | |
| 6,499,851 B1 | 12/2002 | Kelly et al. | |
| 6,619,685 B2 | 9/2003 | Teague | |
| D574,167 S | 8/2008 | Hodge | |
| 7,832,694 B2 | 11/2010 | German et al. | |
| 8,393,749 B1 | 3/2013 | Daicos | |
| 9,304,285 B2 | 4/2016 | Barbour et al. | |
| 2004/0233556 A1 | 11/2004 | LaViola | |
| 2005/0128611 A1 | 6/2005 | Englander | |
| 2012/0228439 A1 * | 9/2012 | Hassid | A47G 25/90 |
| | | | 248/121 |
| 2013/0088154 A1 * | 4/2013 | Van Hoof | H05B 37/02 |
| | | | 315/152 |
| 2014/0262659 A1 * | 9/2014 | Hirsch | A47B 61/06 |
| | | | 190/13 R |
| 2015/0008201 A1 * | 1/2015 | Qiang | A47F 7/24 |
| | | | 211/85.3 |

OTHER PUBLICATIONS

Denis Page, "Which Laptop (or Keyboard) Stand Should I Choose?", Indigo Maple, Aug. 6, 2012 http://www.imc-laptop-stand.com/article-which-laptop-stand-should-i-choose.html.
"AD Mirror System", retrieved on Apr. 29, 2016 at <<http://adproducts.us/adProductsAvailableProducts.html>>.
"AD Mirror System Demonstration", (You Tube), retrieved Apr. 29, 2016, at <<https://www.youtube.com/watch?v=snzW6hn2b4E>>.
"ADproducts Announces Wall Mirror Mounts", retrieved on Apr. 29, 2016 at <<https://www.linkedin.com/pulse/adproducts-announces-wall-mirror-mounts-ron-dolar>>
"Mukava Ergonomic Reading Table", retrieved on Apr. 29, 2016 at <<http://www.mukava-tables.com/>>.
"Pyle PMKSPAD2 Universal Tablet PC/Android/Kindle/iPad Floor Stand Reading", retrieved on Apr. 29, 2016 at <<http://www.amazon.com/Pyle-PMKSPAD2-Universal-Android-Instrument/dp/B009WGPCOW>>.

* cited by examiner

PERSONAL VIEWING DEVICE

CROSS REFERENCE TO RELATED APPLICATIONS

This application claims the benefit of U.S. Provisional Application No. 61/918,561, filed on Dec. 19, 2013, the disclosure of which is incorporated herein by reference in its entirety.

BACKGROUND

Personal viewing devices, such as mirrors, can be used for various purposes and have been used for some time. Some personal viewing devices can be stationary or can be otherwise affixed to other objects such as walls, furniture, or medicine cabinets. Other personal viewing devices can be held in a user's hand to allow personal viewing of various portions of the body. Still other personal viewing devices are not affixed to other objects and are not meant to be held in a user's hand, but instead include supports to allow the device to stand on its own.

The personal viewing devices described above may be difficult for persons with limited mobility or handicaps to use or to perform personal tasks. Such persons may need the assistance of others to personally view their bodies. The ability for personal viewing is particularly limited for persons who have an ostomy or other wound on a portion of their body that is difficult to see or reach. Persons with amputation wounds may also find it difficult to see or reach such wounds.

For ostomy or certain wound care patients specifically, they may have open wounds on their abdomen or on the lower part of their back or buttocks. These ostomy stomas are cleaned multiple times per week and sometimes daily. Personal cleaning of the stoma can be accomplished by emptying a pouch that is attached to the patient and removing it from the skin. Inspection of the skin and cleaning of the stoma allows for easier placement of the new pouch, which can require the use of both of the patient's hands, eliminating the possibility of using a handheld personal viewing device to aid in the viewing of the wound. Additionally, due to the presence of certain types of wounds that are difficult to reach or see, personal viewing of the wound, even with a stationary mirror, is difficult and often requires the assistance of a second person. Personal viewing of certain ostomy wounds can be accomplished using a personal viewing device large enough to view the top portion of the patient's body, but such personal viewing devices are often not portable, can be located in public places not conducive to performing personal cleaning tasks, or would otherwise require a patient to stand, which may be problematic or impossible for some patients. Also, cleaning of ostomy wounds in the standing position is not favorable in light of the possibility that human waste may be expelled from the patient in this position For amputees, viewing of their wounds may require them to be in a seated position, and the nature of their wounds may require a mirror to view. Even when such wounds have healed, the use of a mirror during the placement of prosthetics may be necessary or helpful. A patient with an amputated leg may require the use of both hands, or a patient with an amputated arm may require the use of his or her remaining hand, when cleaning a wound or when applying a prosthetic. Handheld mirrors, therefore, may not be useable, and mirrors that are affixed to walls or other objects limit when and where an amputee may view his or her wound.

SUMMARY

The present disclosure provides a portable, freestanding, adjustable, and deconstructable personal viewing device. The device can include a base member, a mast member, and a branch member that can removably couple to each other, with an appliance, such as a mirror, removably coupled to the branch member to create the personal viewing device. The removable components of the personal viewing device can allow a user to deconstruct the device and transport it as desired.

The personal viewing device can be configured so that the components of the personal viewing device can be removably coupled without the use of screws, rivets, glue, or other fastening means. Instead, the components can be configured to insert into each other to create the personal viewing device. By so doing, users with limited mobility or handicaps can construct or deconstruct the personal viewing device without the aid of tools and with limited dexterity.

The personal viewing device can be configured to allow adjustability of height and position of the appliance, for example a mirror. The mast member can comprise a plurality of rods of varying length to adjust the height of the personal viewing device. The branch member can be configured to rotate about the point where the branch member and mast member meet, which can allow the user to adjust the position of the appliance on the branch member for his or her personal viewing needs.

The personal viewing device can also be configured so that the personal viewing device, when constructed, can stand without the aid of the user or an assistant. The base member can also be configured to fit beneath a bed or other object that allows the user to lie in a supine position. The branch member can be adjusted to extend over or next to a user while in the supine position to facilitate personal viewing.

The personal viewing device will become more readily appreciated and understood from a consideration of the following detailed description of the exemplary embodiments of the present disclosure when taken together with the accompanying drawings.

FIGURES

Various embodiments of the present invention are described herein by way of example in connection with the following figures, wherein.

DESCRIPTION

The present invention will now be described to provide an overall understanding of the principles of the structure, function, manufacture, and use of the devices and methods disclosed herein. One or more examples of the present invention are illustrated in the accompanying drawings. Those of ordinary skill in the art will understand that the devices and methods specifically described herein and illustrated in the accompanying drawings are non-limiting embodiments and that the scope of these embodiments is defined solely by the claims. The features illustrated or described in connection with one embodiment may be combined with the features of other embodiments. Such modifications and variations are intended to be included within the scope of the appended claims.

In general, the present invention is directed to a portable, freestanding, adjustable, and deconstructable personal viewing device as can be seen in FIGS. 1-14.

Figure 7:
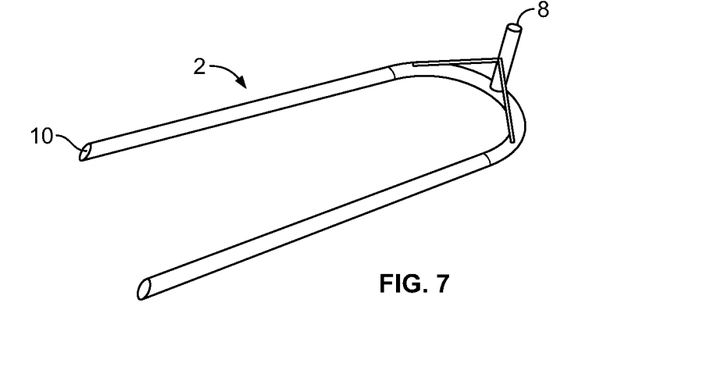
FIG. 7 is a perspective view of a base member.

As seen in FIGS. 1-4, the personal viewing device can comprise a base member 2, a mast member 4, and a branch member 6. The base member 2 can be removably coupled to the mast member 4, and the mast member 4 can be removably coupled to the branch member 6. The mast member 4 can be excluded from the personal viewing device such that the base member 2 and the branch member 6 can be removably coupled. The base member 2 can be configured as a substantially U-shaped or V-shaped rod. The base member 2 can be a variety of shapes and can have one or more bends. The base member 2 can by substantially U-shaped or V-shaped, but the ends of the base member 2 can extend outward such that the width of the base member 2 is greater than a base member 2 with ends that do not extend outward. The rod can be cylindrical in geometry and can have a range of diameters and can be varying lengths. The rod can also be configured to telescope such that the legs of the base member 2 can be compressed and therefore shortened, or the legs of the base member 2 can be extended and therefore elongated. The bend in the rod can be configured to include a stud 8 extending substantially perpendicularly from the rod (as shown in FIG. 7). The rod that makes up the base member 2 can have beveled ends 10 opposite the bend in the rod. The base member 2, mast member 4, and branch member 6 can be made from one or multiple pieces of material, such as metal.

Figure 8:
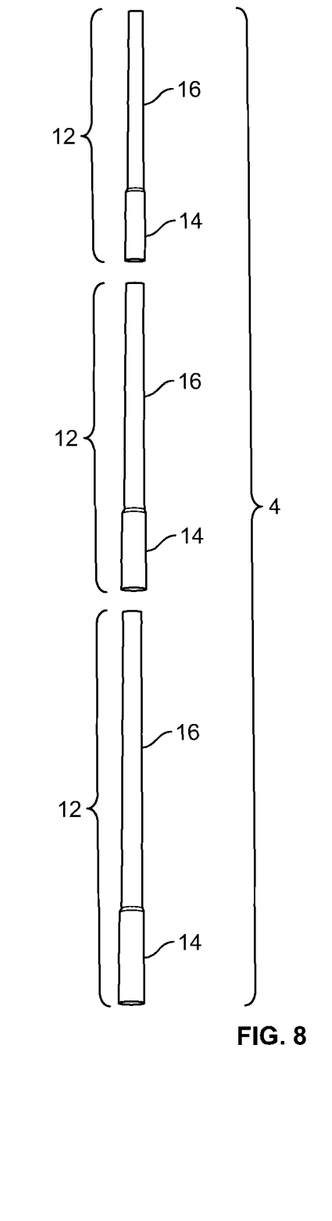
FIG. 8 is a side view of a plurality of rods making up a mast member.

Still referring to FIGS. 1-4, the mast member 4 of the personal viewing device can be made up of a plurality of rods 12 of varying lengths (also shown in FIG. 8). The rods 12 can have a sleeved end 14 and an unsleeved end 16. The rods 12 can be configured such that the unsleeved end 16 of one rod 12 can be inserted into the sleeved end 14 of another rod 12. The rods 12 can be configured such that the unsleeved end 16 of one rod 12 can fit completely or partially into the sleeved end 16 of another rod 12. When engaged, the rods 12 that make up the mast member 4 can remain engaged without the use of fasteners, such as rivets, screws, glue, or clamps. The rods 12 can be disengaged from each other by sliding the sleeved end 14 of one rod 12 off of the unsleeved end 16 of another rod 12. The mast member 4 can be removably coupled to the base member 2 by inserting the stud 8 from the base member 2 into the sleeved end 14 of one rod 12 of the mast member 4. The stud 8 and the rods 12 can be a variety of diameters and lengths. The embodiment of the present invention shown in FIGS. 1-4 shows one mast member 4 with one branch member 6 removably coupled thereto. However, it is to be understood that in various other embodiments of the present invention multiple mast members 4 could be removably coupled to the base member 2, with each mast member 4 having a branch member 6. The rods 12 of the mast member 4 can be interchangeably coupled to each other such that the sleeved end 16 of one rod 12 can fit the unsleeved end 14 of any of the other rods 12, and the unsleeved end 14 of one rod 12 can fit into the sleeved end 16 of any of the other rods 12.

The mast member 4 can telescope such that the rods 12 that make up the mast member 4 can be coupled and can extend and retract to create varying lengths of the mast member 4. The rods 12 of the mast member 4 can be configured to include a camlock or other fastening means such that when the rods 12 are coupled together, the camlock or other fastening means can be used to secure one rod 12 to another rod 12.

Still referring to FIGS. 1-4, the branch member 6 of the personal viewing device can be comprised of a proximal, sleeved end 18 and a distal end 20. The branch member 6 can be removably coupled to the mast member 4 by inserting the unsleeved end 16 of one rod 12 of the mast member 4 into the proximal, sleeved end 18 of the branch member 6. The branch member 6 can be bent or curved such that the portion of the branch member 6 making up the distal end 20 can be substantially perpendicular to the proximal, sleeved end 18 of the branch member 6. The embodiment of the present invention as shown in FIGS. 1-4 shows a substantially 90 degree curve in the branch member 6. However, other embodiments of the present invention, not shown herein, can have a range of curves or can have no curve at all. The distal end 20 of the branch member 6 can be configured to include an appliance 22, such as a mirror. At least a portion of the branch member 6 can be configured to telescope such that the branch member 6 can be elongated or shortened.

The components described above in the present disclosure and as shown in FIGS. 1-4 can be removably coupled without the use of screws, rivets, nuts and bolts, or other fastening or locking means. The sleeved and unsleeved ends of the various components described above can be honed, tapered, or conical in design as opposed to cylindrical. Each of the components described above can be removed from the other components without damage to the personal viewing device and with minimal dexterity or efforts by the user.

As seen in FIGS. 1-4, when the base member 2, the mast member 4, and the branch member 6 are removably coupled together to form the personal viewing device, the device can be freestanding with the base member 2 making contact with a floor or other similar surface.

Figure 1:
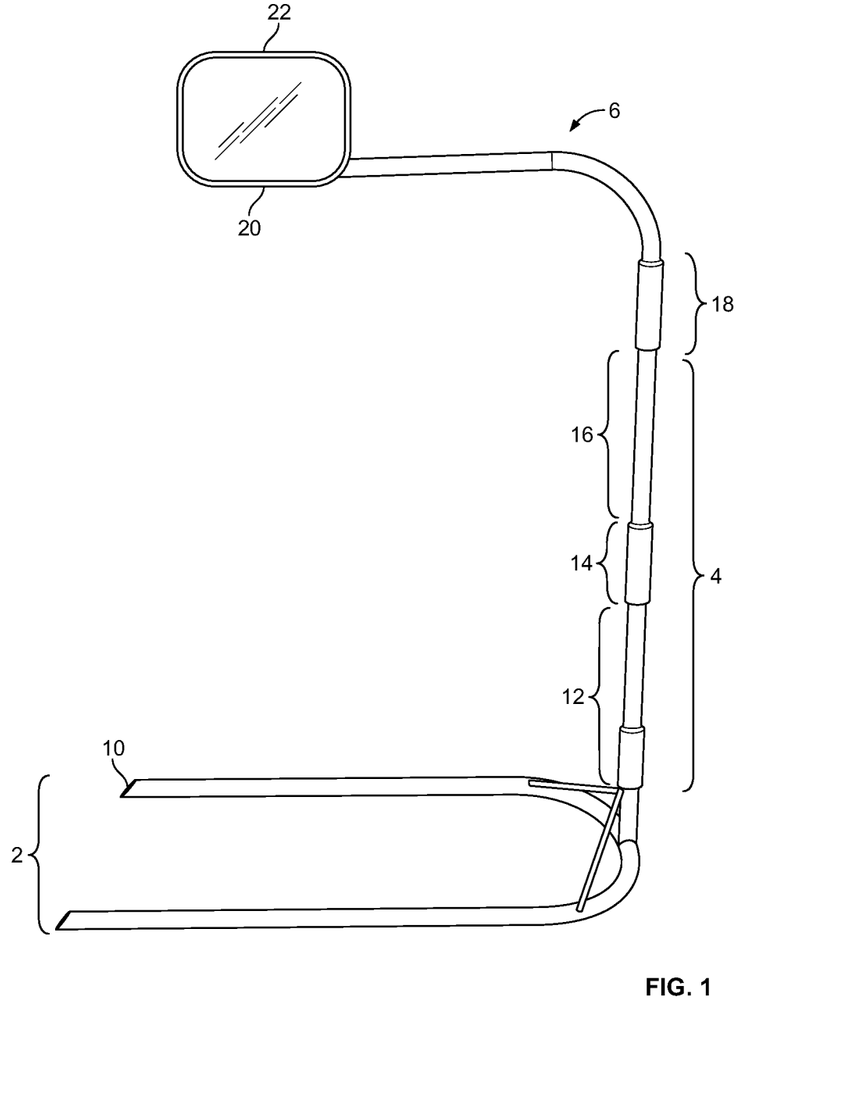
FIG. 1 is a side view of a personal viewing device.
Figure 2:
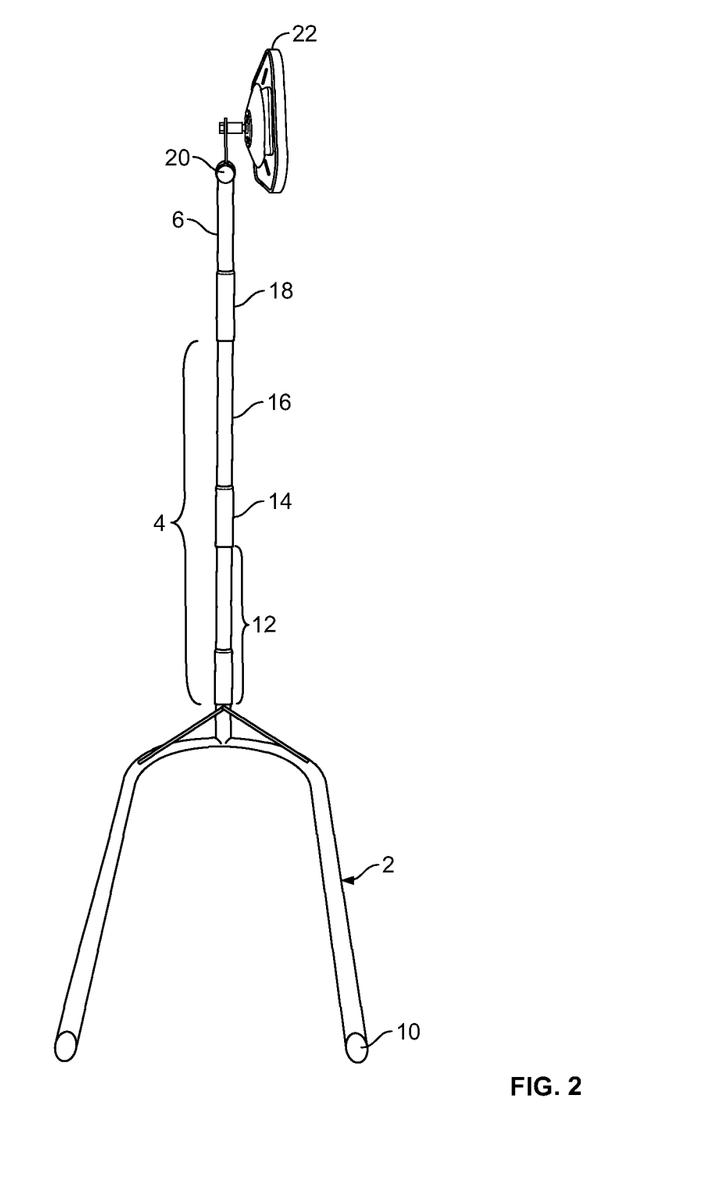
FIG. 2 is a frontal view of a personal viewing device.
Figure 3:
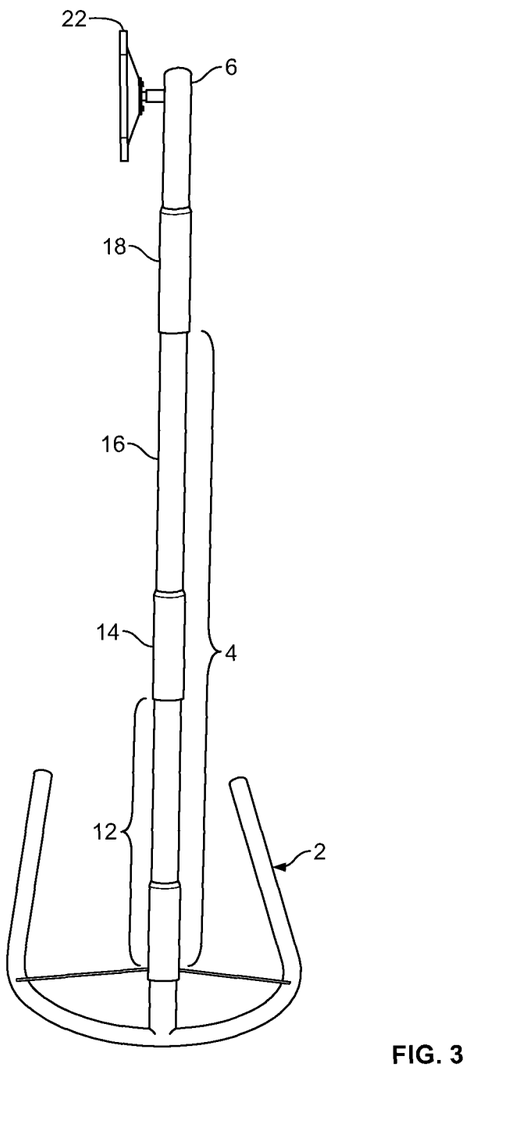
FIG. 3 is a rear view of a personal viewing device.
Figure 4:
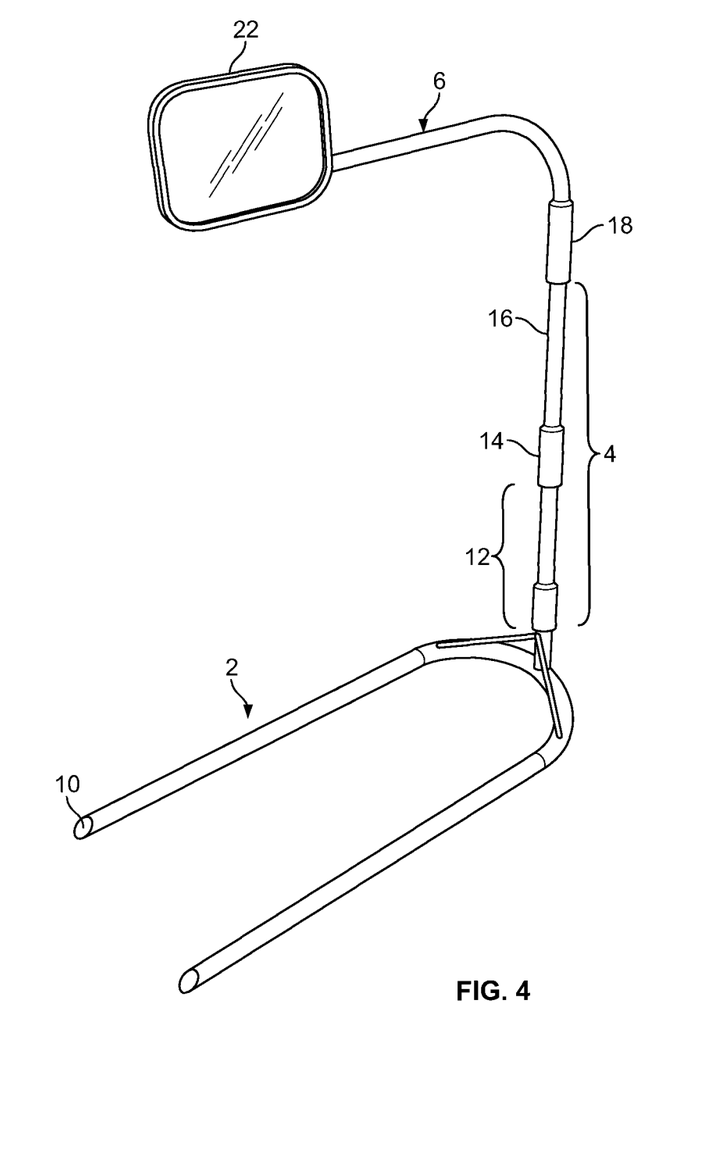
FIG. 4 is a perspective view of a personal viewing device.
Figure 5:
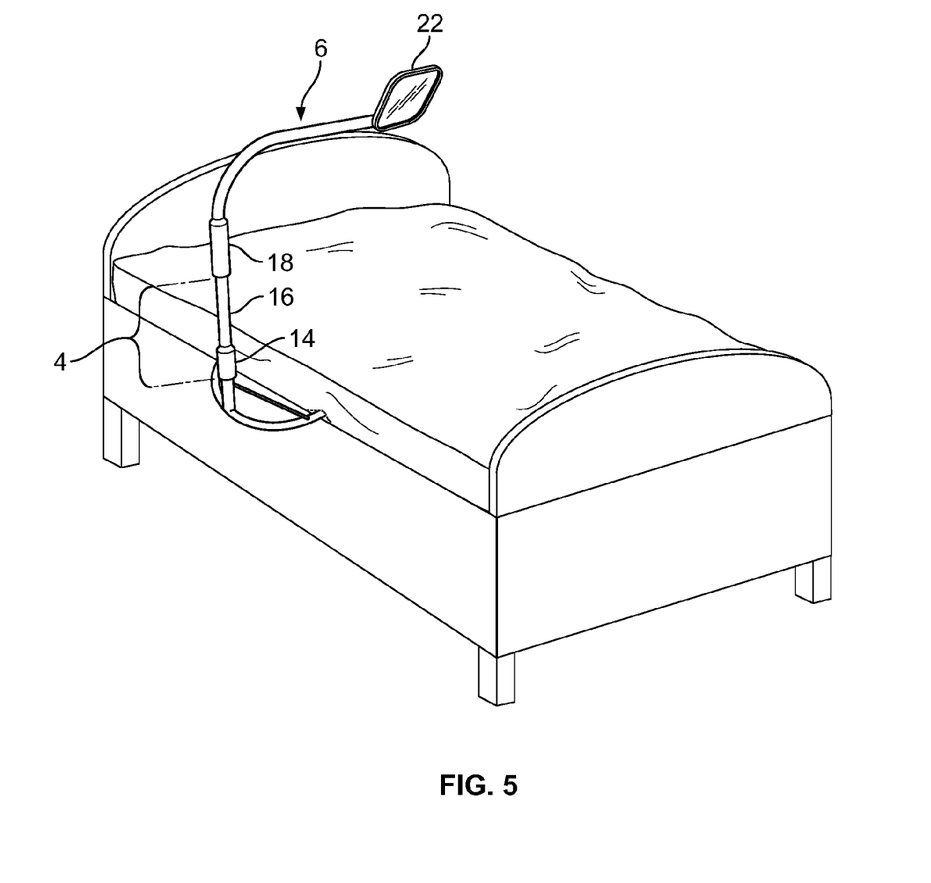
FIG. 5 is a perspective view of a personal viewing device in use.

As seen in FIG. 5, when the base member 2, the mast member 4, and the branch member 6 are removably coupled together to form the personal viewing device, the base member 2 can be inserted beneath a bed, mattress, or other flat surface, allowing the mast member 4 to extend upwards next to the bed, mattress, or other flat surface, and allowing the branch member 6 to extend above and over the bed, mattress, or other flat surface. The beveled ends 10 can aid in inserting the base member 2 of the personal viewing device between two objects, such as between a mattress and a box spring. The branch member 6 can rotate about the point where the branch member 6 is coupled to the mast member 4, such that a patient, when in a supine position, can rotate the branch member 6 over his or her body or can rotate the branch member 6 away from his or her body. The ability to rotate the branch member 6 can allow the patient to use the appliance 22 on the branch member 6 when desired, and then move the branch member 6 away from him or herself when not in use.

Figure 6:
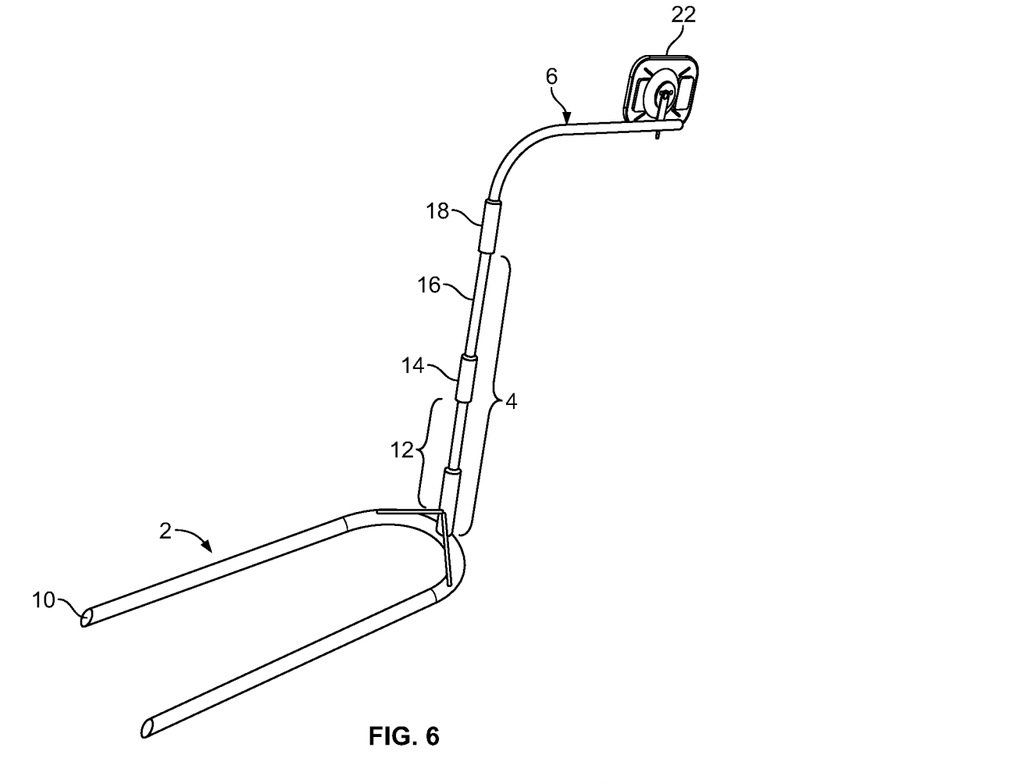
FIG. 6 is a perspective view of a personal viewing device with a rotated branch member.

As seen in FIG. 6, the branch member 6 can rotate about the point where the proximal sleeved end 18 of the branch member 6 meets with the mast member 4. As shown in FIGS. 1-4, the branch member 6 can be positioned such that the branch member 6 is substantially over top of and parallel to the base member 2. As shown in FIG. 6, the branch member 6 can be positioned to be rotated 180 degrees from the position shown in FIGS. 1-4 such that the branch member 6 extends from the mast member 4 in the opposite direction of the base member 4. The branch member 6 can also be rotated at any angle about the point where the branch member 6 meets with the mast member 4. As shown in FIG. 6, even with the branch member 6 positioned 180 degrees in the opposite direction of the base member 4, the personal viewing device can be freestanding. The rotatable branch member 6 can allow for a user to view him/herself from a number of standing, sitting, or supine positions.

Figure 9:
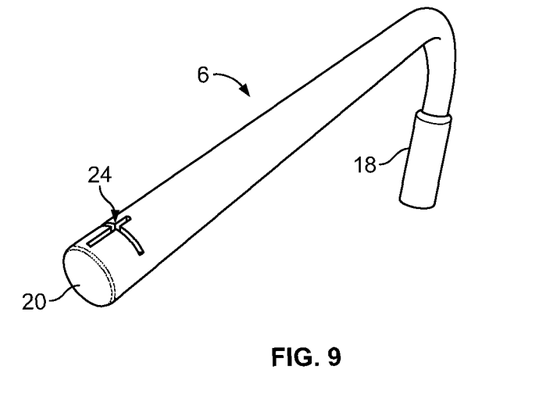
FIG. 9 is a perspective view of a branch member.

As seen in FIG. 9, the distal end 20 of the branch member 6 can have one or more slits 24 capable of receiving an appliance 22. As shown in FIG. 9, the distal end 20 of the branch member 6 has two slits 24 positioned substantially on the top side of the branch member 6. The width and length of the slits 24 can vary depending on the desired application and the desired appliance 22 to be removably coupled to the branch member 6. While the invention shown in FIG. 9 shows the slits 24 as narrow grooves, it is to be understood that any geometric configuration of the slits 24 can be used in the branch member 6. Additionally, while the slits 24 as shown in FIG. 9 are depicted on the distal end 20 of the branch member 6, the slits 24 can also be placed at any position between the distal end 20 and the curve in the branch member 6. Furthermore, multiple slits 24 can be included on a branch member 6 to removably couple to multiple appliances 22, or to allow an appliance 22 to be placed in one of multiple locations on the branch member 6. This can allow the personal viewing device to be used for multiple purposes and allow for various device sizes. The appliance 22 can also be affixed to the branch member 6, such as by soldering, screws, and other fastening means. The slits 24 can also be placed on the sides, bottom, and end of the branch member 6. The slits 24 can also extend through the top and bottom of the branch member 6 such that when the appliance 22 is received by the slits 24, at least a portion of the appliance 22 can be inserted through the slits 24 from the top of the branch member 6, extending through the branch member and out the bottom of the slits 24 on the bottom of the branch member 6. The distal end 20 of the branch member 6 may also include a post or stud configured to receive at least a portion of the appliance 22.

Figure 10:
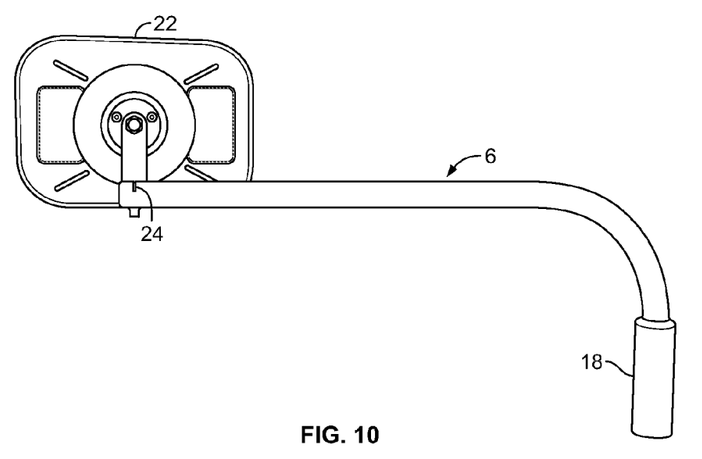
FIG. 10 is a side view of a branch member.
Figure 11:
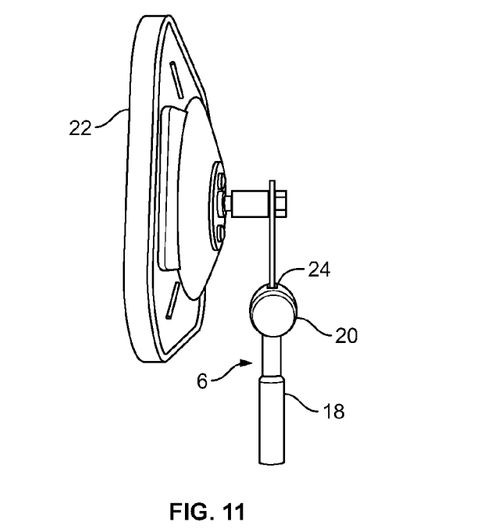
FIG. 11 is an end view of a branch member.

As shown in FIGS. 10-11, the appliance 22 can be removably coupled to the branch member 6 on the branch member's distal end 20. As shown in FIGS. 10-11, the appliance 22 is a mirror. Other appliances 22, not shown herein, can be used in the place of or in addition to a mirror, such as a flashlight. The appliance 22 can be affixed to the branch member 6 by soldering, screws, or other fasteners.

Figure 12:
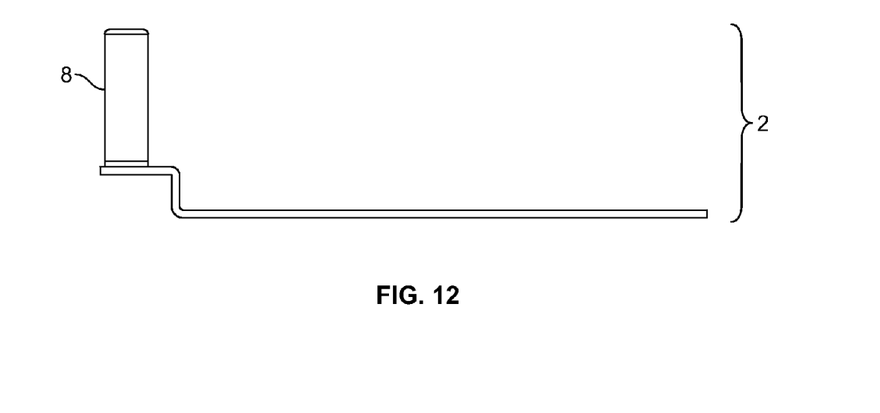
FIG. 12 is a side view of a branch member for application with a bed mattress or other flat surface.

As shown in FIG. 12, the base member 2 can include a rod configured in geometries other than cylindrical. The rod of the base member 2 can be substantially flat. A flat base member 2 can allow a patient to more easily slide the base member 2 between two flat surfaces, such as between a mattress and a bed frame or a mattress and a floor. Like the base member 2 discussed above with a cylindrically shaped rod, the base member depicted in FIG. 12 can be removed from the mast member 4 with limited dexterity. The present invention can include at least two base members 2, one with a cylindrically shaped rod and one with a flat rod, and the two base members 2 can be used interchangeably.

Figure 13:
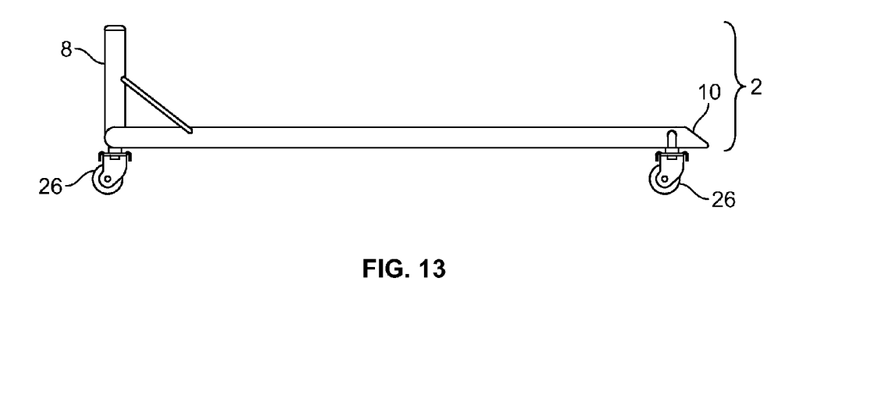
FIG. 13 is a side view of a branch member with wheels.

Referring next to FIG. 13, the base member 2 can be configured to include one or more wheels 26 on the bottom of the base member 2. The wheels 26 can allow the personal viewing device to be rolled from one area to another, such as from a bedroom to a bathroom. The wheels 26 can be affixed to the base member 2, such as by soldering, screws, or other fastening means. The wheels 26 can also be removably coupled to the base member 26 such that a patient who did not desire the use of the wheels 26 could remove them to achieve a configuration shown in FIGS. 1-4.

Figure 14:
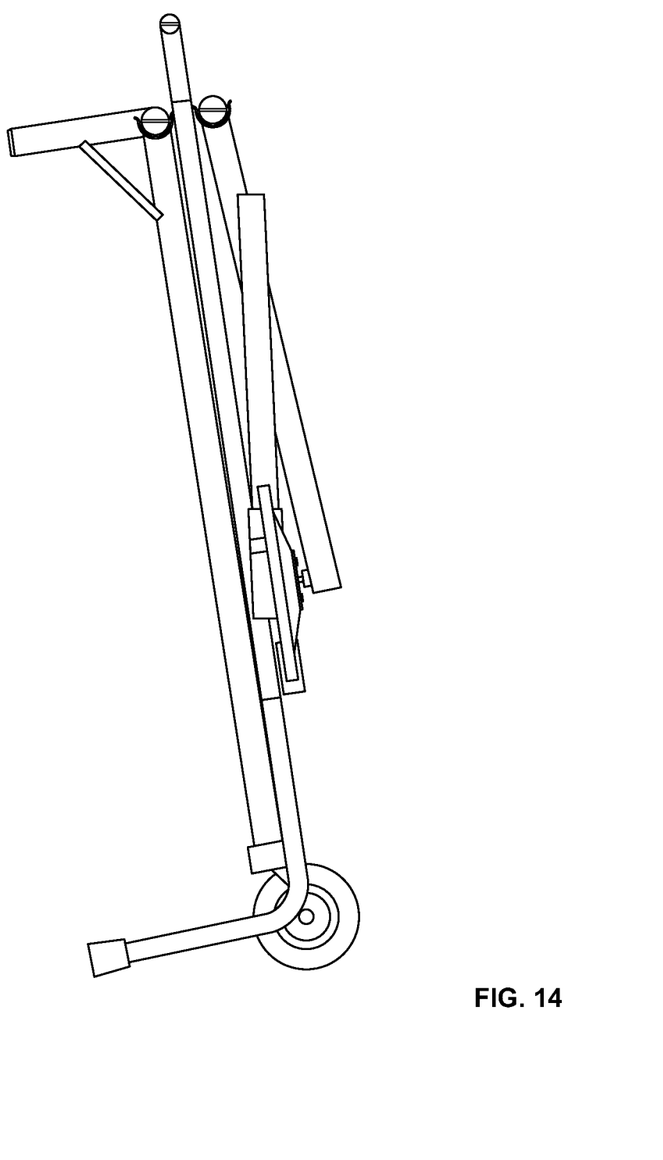
FIG. 14 is a side view of a caddy.

As described above, the various elements of the personal viewing device described herein can be removably coupled to each other, such that each of the elements can be removed as individual elements. When the personal viewing device is disassembled, its components can be stored in a bag, a case, or on a caddy, for example. As shown in FIG. 14, a caddy configured to receive the components of the personal viewing device is shown. The caddy can have receptacles capable of receiving and storing the base member 2, the mast member 4, and the branch member 6. The caddy can be configured to include wheels such that the caddy can be transported with or without the components of the personal viewing device stored on it.

Also as described above, the personal viewing device described herein can be of varying sizes and scales. For example, the personal viewing device may be approximately four to five feet tall when its various elements are removably coupled. The personal viewing device can also be scaled down such that the device is one foot tall when its various elements are removably coupled.

The present disclosure can be made of one or more of various materials, including but not limited to metal and plastic. When made of metal, the present disclosure can be made of any metal with suitable strength and malleability, such as steel, to create the device described herein. The rods making up the base member 2, mast member 4, and branch member 6 can be hollow to allow for a lighter personal viewing device. The bends in the base member 2 and branch member 6, as described above and as shown in the Figures hereto can be formed using techniques known to those having skill in the art of metal working. The stud 8 can be affixed to the base member 2 such as by soldering. The slits 24 in the branch member 6 can be made by grinding or tooling grooves into the branch member 6 in the locations described above. When made using plastics, polymeric material can be injection molded to create the components of the personal viewing device.

In use, the various components of the personal viewing device can be assembled in any order. By way of example, the unsleeved end 16 of one rod 12 making up the mast member 4 can be received by the sleeved end 14 of another rod 12, such that two rods 12 make up the mast member 4. The unsleeved end 16 of the top rod 12 can make up the top of the mast member 4 and the sleeved end 14 of the bottom rod 12 can make up the bottom of the mast member 4. The mast member 4 can then be removably coupled to the base member 2 by sliding the sleeved end 14 of the bottom rod 12 from the mast member 4 over the stud 8 on the base member 2. The branch member 6 can then be removably coupled to the mast member 4 by sliding the unsleeved end 16 of the top rod 12 from the mast member 4 into the sleeved end 18 of the branch member 6. The appliance 22 can then be removably coupled to the branch member by inserting a portion of the appliance 22 into the slits 24 on the distal end 20 of the branch member 6.

When assembled, the personal viewing device can be freestanding. When the appliance 22 is a mirror, the mirror can swivel or pivot such that a patient can view his or herself from a number of angles. The patient may then position him or herself in the seated or standing position to view the desired area of the body, rotating the branch member 6 and pivoting the mirror as desired. The patient may also place the base member 2 beneath a bed or other surface such that the branch member 6 extends above the bed. The patient may then lie in the supine position on the bed or other surface, rotate the branch member 6 over the desired area of his or her body, and pivot the mirror to view him or herself.

When the patient has finished using the personal viewing device, the patient may leave the device assembled or may choose to disassemble the device. The personal viewing device can be disassembled in the same order as described above or in a different order by sliding the sleeved ends of the various components off of the unsleeved ends of neighboring components.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

In one general aspect, the present disclosure is directed to a personal viewing device that can comprise a base member for resting on a resting surface, wherein the base member can be coupled to a mast member that extends from the base member in a direction that is not parallel to the resting surface. The mast member can be coupled to a branch member that extends from the mast member, wherein the branch member can comprise a first portion that extends in a direction that is not parallel to the direction that the mast member extends from the base member and parallel to the resting surface. The base member can comprise a bent rod that rests on the resting surface with a stud extending from the bent rod, and with the mast member coupled to the stud of the base member. The mast member can comprise two or more rods each having a sleeved end and an unsleeved end, and the two or more rods can be coupled to each other by inserting the unsleeved end of one rod into the sleeved end of another rod. The branch member can comprise a sleeved end that couples to the unsleeved end of the rods that make up the mast member. The branch member can hold at least one appliance, and the base member, mast member, branch member, and appliance can be assembled without the use of a tool.

In various implementations, the base member, mast member, branch member, and appliance can be removably coupled without screws, rivets, nuts and bolts, or other fasteners. Also, the base member can be substantially U-shaped with the stud situated in the bend of the base member. The branch member may also comprise a proximal end that removably couples to the mast member, and a distal end that can removably couple to the appliance, wherein the distal end of the branch member can include at least one slit and the appliance can be at least partially received by the slit of the branch member. Furthermore, the appliance can be a mirror or a light. Also, the mast member can be substantially perpendicular to the base member when the mast member and the base member are removably coupled, and the branch member can have a sleeved end that removably couples to the mast member wherein the branch member can comprise a bend near the sleeved end such that at least a portion of the branch member is substantially parallel to the base member. The bent rod of the base member can comprise beveled ends, and the base member, mast member, and branch member, when removably coupled, can be freestanding. The base member can fit under a flat surface or between two surfaces. The branch member, when removably coupled to the mast member can rotate with the point of rotation at the junction between the branch member and mast member. The base member, mast member, and branch member can comprise steel rods, with the rods having an at least partially hollow interior. Also, the bent rod of the base member can be substantially flat. The base member can also comprise at least one wheel extending from the base member opposition the direction of the stud.

In another general aspect, the present disclosure is directed a personal viewing device comprising a base member for resting on a resting surface, wherein the base member can be coupled to a branch member that extends from the mast member and the branch member can comprise a first portion that extends in a direction that is parallel to the base member. The branch member can be further configured to hold at least one mirror, and when coupled, the base member and branch member can be freestanding.

In various implementations, the mirror can swivel about the point where the mirror meets the branch member. Also, the base member can comprise a bent rod with a stud extending from the bent rod with the mast member coupled to the stud of the base member, and wherein the branch member can include a sleeved end that couples to the stud of the base member.

In another general aspect, the present disclosure is directed to a personal viewing device comprising a base member for resting on a resting surface, wherein the base member can be removably coupled to a mast member that extends from the base member and is not parallel to the resting surface. The mast member can be removably coupled to a branch member that extends from the mast member, wherein the branch member can comprise a first portion that extends in a direction that is not parallel to the direction that the mast member extends from the base member. Also, the branch member can hold at least one appliance, and the base member, mast member, and branch member can disassemble from each other without the use of a tool. When disassembled, the base member, mast member, and branch member can fit into a moveable container.

In various implementations, the moveable container can be no larger than a backpack.

What is claimed is:

1. A personal viewing device comprising:
   a base member for resting on a resting surface, wherein the base member is coupled to a mast member that extends from the base member in a direction that is not parallel to the resting surface;
   the mast member coupled to a branch member that extends from the mast member, wherein the branch member comprises a first portion that extends in a direction that is not parallel to the direction that the mast member extends from the base member and parallel to the resting surface;
   the base member comprises a bent rod that rests on the resting surface with a stud extending from the bent rod, and with the mast member coupled to the stud of the base member;

the mast member comprising two or more rods each having a sleeved end and an unsleeved end, and the two or more rods coupled to each other by inserting the unsleeved end of one rod into the sleeved end of another rod;

the branch member comprising a sleeved end that couples to the unsleeved end of a rod of the two or more rods that make up the mast member;

the branch member further configured to hold at least one appliance, wherein the at least one appliance is a mirror, wherein the mirror swivels about a point where the mirror meets the branch member; and the base member, mast member, branch member, and appliance are assembled without the use of a tool, wherein the base member, mast member, branch member and appliance are removably coupled without screws, rivets, nuts and bolts, or other fasteners.

2. The device of claim 1, wherein:

the branch member comprises a proximal end that removably couples to the mast member, and a distal end that removably couples to the appliance;

the distal end of the branch member includes at least one slit; and the appliance is at least partially received by the slit of the branch member.

3. The device of claim 1, wherein the base member is substantially U-shaped with the stud situated in the bend of the base member.

4. The device of claim 1, wherein the at least one appliance includes a light.

5. The device of claim 1, wherein:

the mast member is substantially perpendicular to the base member when the mast member and the base member are coupled; and the sleeved end of the branch member removably couples to the mast member, and the branch member comprises a bend near the sleeved end such that at least a portion of the branch member is substantially parallel to the base member.

6. The device of claim 1, wherein the bent rod of the base member comprises beveled ends.

7. The device of claim 1, wherein the base member, mast member, and branch member, when removably coupled, are freestanding.

8. The device of claim 1, wherein the base member fits under a flat surface.

9. The device of claim 1, wherein the base member fits between two surfaces.

10. The device of claim 1, wherein the branch member, when removably coupled to the mast member, rotates with the point of rotation at the junction between the branch member and mast member.

11. The device of claim 1, wherein the base member, mast member, and branch member comprise steel rods, with the rods having an at least partially hollow interior.

12. The device of claim 1, wherein the base member, mast member, and branch member are configured to disassemble from each other without use of a tool.

13. The device of claim 12, wherein the base member, mast member, and branch member, when disassembled, are sized to fit into a moveable container.

14. The device of claim 13, wherein the moveable container is no larger than a backpack.

* * * * *